(12) United States Patent
Pepe et al.

(10) Patent No.: US 12,070,262 B2
(45) Date of Patent: Aug. 27, 2024

(54) ELECTROSURGICAL DEVICE WITH VACUUM PORT

(71) Applicant: Buffalo Filter LLC, Lancaster, NY (US)

(72) Inventors: Gregory Pepe, Lancaster, NY (US); Michael J. Miller, Depew, NY (US); Kyrylo Shvetsov, Depew, NY (US); Samantha Bonano, Williamsville, NY (US)

(73) Assignee: Buffalo Filter LLC, Lancaster, NY (US)

( * ) Notice: Subject to any disclaimer, the term of this patent is extended or adjusted under 35 U.S.C. 154(b) by 497 days.

(21) Appl. No.: 15/484,927

(22) Filed: Apr. 11, 2017

(65) Prior Publication Data

US 2017/0290628 A1    Oct. 12, 2017

Related U.S. Application Data

(60) Provisional application No. 62/320,867, filed on Apr. 11, 2016.

(51) Int. Cl.
*A61B 18/14*  (2006.01)
*A61B 18/00*  (2006.01)

(52) U.S. Cl.
CPC .......... *A61B 18/1485* (2013.01); *A61B 18/14* (2013.01); *A61B 18/1402* (2013.01);
(Continued)

(58) Field of Classification Search
CPC ............ A61B 18/1485; A61B 18/1402; A61B 2018/00964; A61B 2218/008;
(Continued)

(56) References Cited

U.S. PATENT DOCUMENTS

| | | | |
|---|---|---|---|
| 5,445,142 A * | 8/1995 | Hassler, Jr. | ........ A61B 1/00087 600/105 |
| 5,451,222 A | 9/1995 | De Maagd et al. | |

(Continued)

FOREIGN PATENT DOCUMENTS

| | | |
|---|---|---|
| EP | 2679192 A2 | 1/2014 |
| EP | 2789307 A1 | 10/2014 |

(Continued)

OTHER PUBLICATIONS

International Search Report and Written Opinion from corresponding PCT/US2017/027021, completed May 30, 2017 (8 pages).

(Continued)

*Primary Examiner* — Khadijeh A Vahdat
(74) *Attorney, Agent, or Firm* — Timothy W. Menasco, Esq.; Harter Secrest & Emery LLP

(57) ABSTRACT

Presented are a method and apparatus for surgical procedures. An exemplary apparatus includes a body having a longitudinal axis and a connection opening at a first end of the longitudinal axis, the connection opening including an electrical connection to an electrical circuit maintained within the body and an air path extending through the longitudinal axis of the body. The apparatus further includes a tube assembly having a distal end and a mating end along a tube longitudinal axis, the tube assembly having a vacuum inlet circumscribing an electrode extending from the distal end, the vacuum inlet operable for receiving surgical smoke, the vacuum inlet fluidly connected to an air tube extending through the tube longitudinal axis, the mating end operable to be removably affixed to the connection opening thereby connecting the electrode with the electrical connection and the air path with the air tube, and a first button.

17 Claims, 13 Drawing Sheets

(52) U.S. Cl.
CPC .............. *A61B 2018/00964* (2013.01); *A61B 2018/1475* (2013.01); *A61B 2218/008* (2013.01)

(58) Field of Classification Search
CPC ........... A61B 18/14; A61B 2018/1475; A61M 25/0026; A61M 2005/2073; A61M 1/0041
See application file for complete search history.

(56) References Cited

U.S. PATENT DOCUMENTS

| | | | |
|---|---|---|---|
| 5,674,219 | A | 10/1997 | Monson et al. |
| 8,057,470 | B2 | 11/2011 | Lee et al. |
| 8,641,488 | B1 | 2/2014 | Shvetsov et al. |
| 9,289,261 | B2 | 3/2016 | Shvetsov et al. |
| 2003/0181904 | A1* | 9/2003 | Levine ............... A61B 18/1402 606/45 |
| 2004/0034339 | A1* | 2/2004 | Stoller ................ A61B 1/3132 606/1 |
| 2004/0039373 | A1* | 2/2004 | Harding ............ A61M 25/0014 604/533 |
| 2006/0264928 | A1* | 11/2006 | Kornerup ........... A61B 18/1402 606/45 |
| 2007/0049927 | A1* | 3/2007 | Saltzman ........... A61B 18/1402 606/45 |
| 2009/0062791 | A1* | 3/2009 | Lee .................... A61B 18/1402 606/45 |
| 2011/0190768 | A1 | 8/2011 | Shvetsov et al. |
| 2011/0301578 | A1 | 12/2011 | Muniz-Medina et al. |
| 2012/0116433 | A1* | 5/2012 | Houser .............. A61B 18/1445 606/169 |
| 2012/0283728 | A1* | 11/2012 | Cosmescu ............. A61B 90/35 606/46 |
| 2013/0261610 | A1 | 10/2013 | Laconte et al. |
| 2013/0345701 | A1* | 12/2013 | Allen, IV ............. A61B 18/082 606/41 |
| 2014/0081086 | A1* | 3/2014 | Shvetsov ............... A61B 90/30 600/249 |
| 2014/0276763 | A1 | 9/2014 | Greep et al. |
| 2015/0112323 | A1* | 4/2015 | Hagg .................... A61B 18/14 606/34 |
| 2015/0335376 | A1 | 11/2015 | Hufnagel et al. |
| 2016/0157918 | A1 | 6/2016 | Shvetsov et al. |

FOREIGN PATENT DOCUMENTS

| | | |
|---|---|---|
| WO | 2004054626 A2 | 7/2004 |
| WO | 2010098809 A3 | 9/2010 |

OTHER PUBLICATIONS

Extended European Search Report from corresponding EP 17782984.3, completed Sep. 27, 2019 (11 pages).

International Search Report and Written Opinion of The International Searching Authority PCT/US2015/021008 (7 pages) Jul. 11, 2016.

* cited by examiner

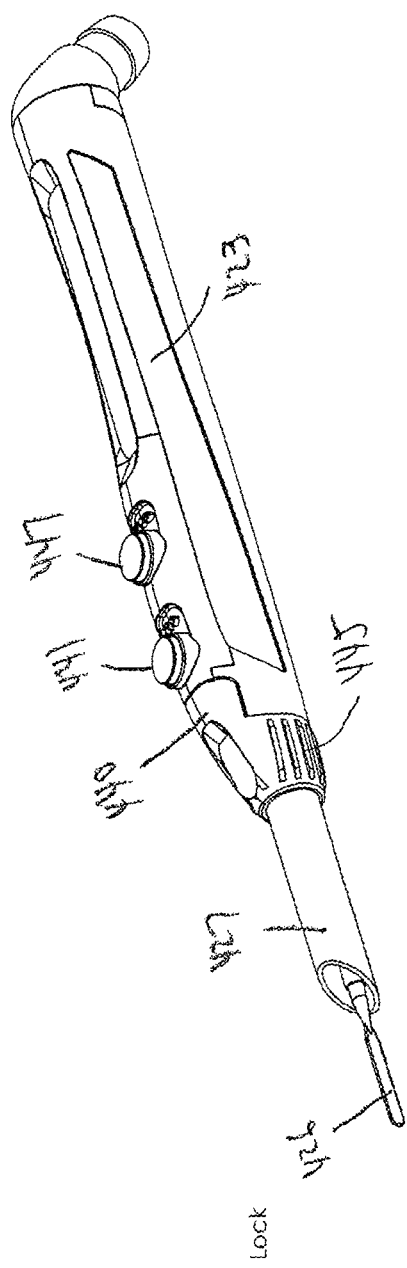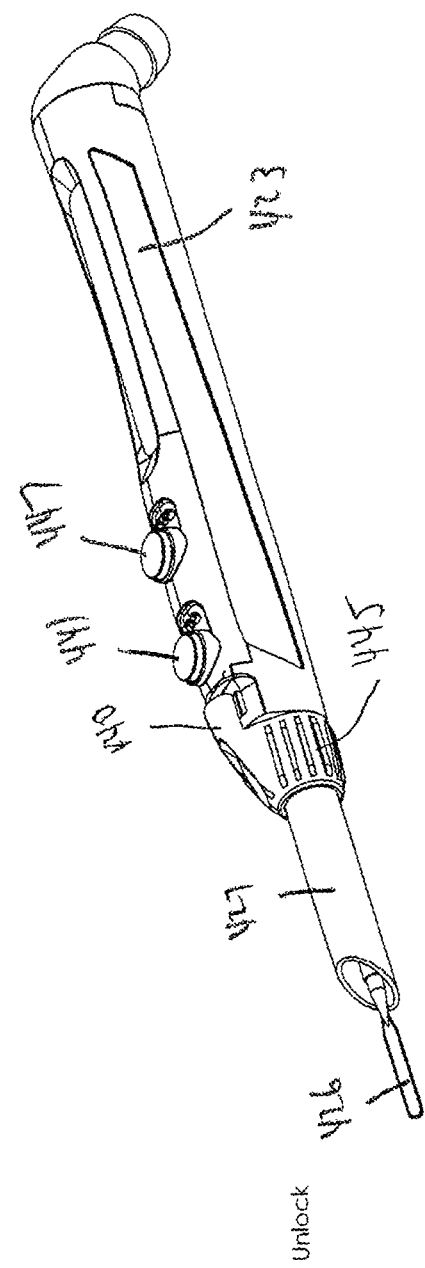

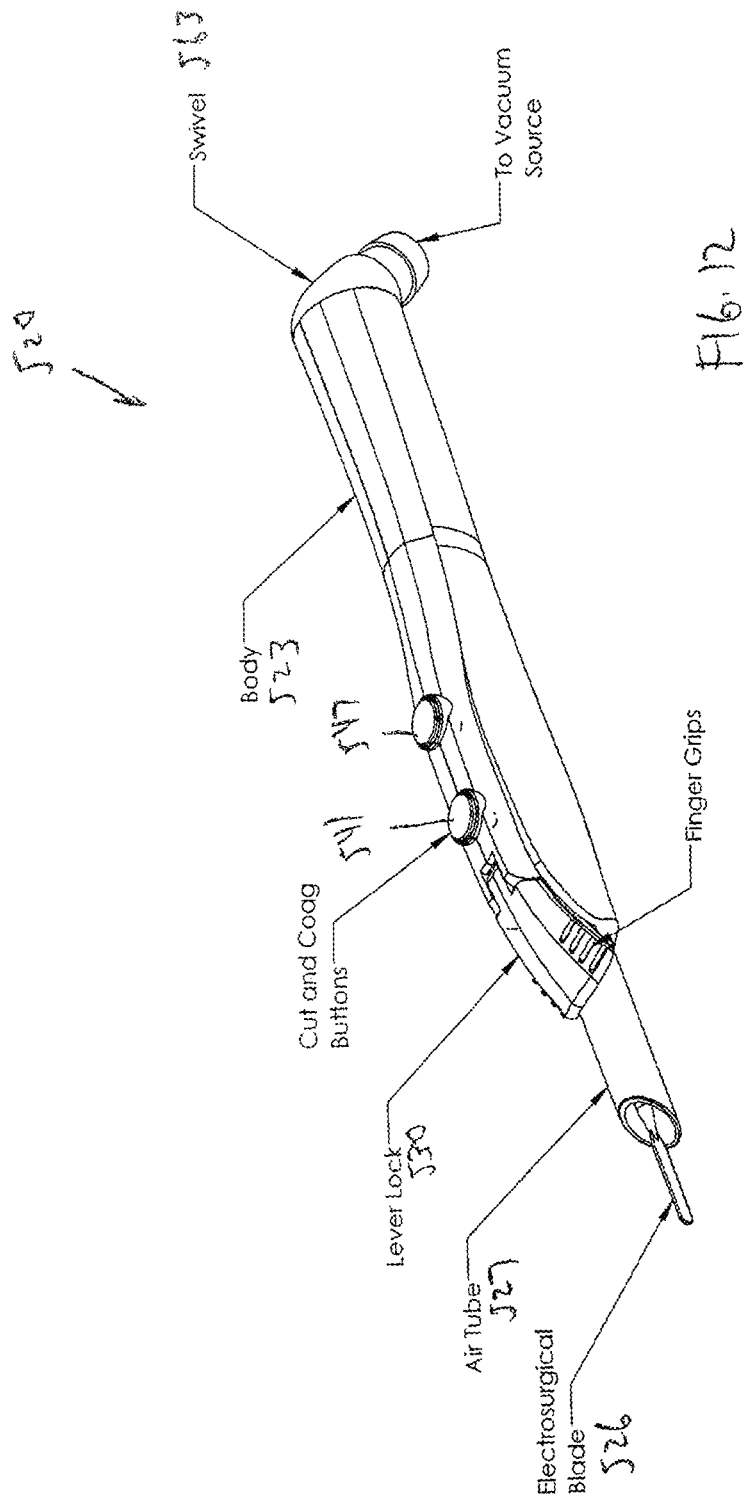

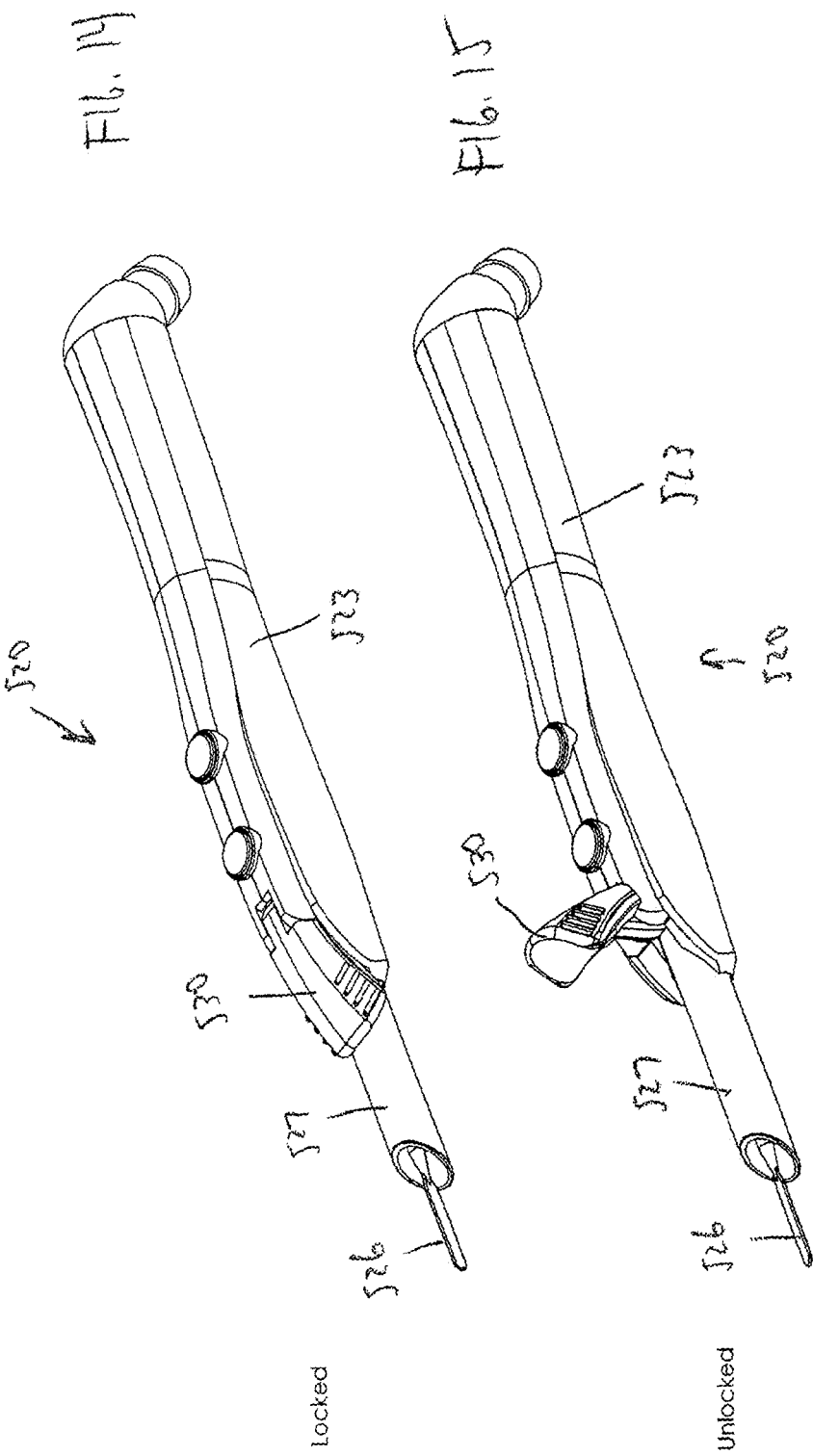

ELECTROSURGICAL DEVICE WITH VACUUM PORT

BACKGROUND OF THE INVENTION

Field of the Invention

The present invention relates generally to smoke evacuation, and, more specifically, to an electrosurgical device with smoke evacuation during medical procedures.

Description of Related Art

Surgical smoke and aerosol, or plume, is created in connection with surgery. For example, when laser or electrosurgical energy is delivered to a cell, heat is created. This heat vaporizes the intracellular fluid, which increases the pressure inside the cell and eventually causes the cell membrane to burst. In this example, a plume of smoke containing water vapor is released into the atmosphere of the operating room or doctor's office. At the same time, the heat created may char the protein and other organic matter within the cell, and may cause thermal necrosis in adjacent cells. The charring of cells may also release other harmful contaminants, such as carbonized cell fragments and gaseous hydrocarbons.

BRIEF SUMMARY OF THE INVENTION

In view of the foregoing, it is an object of the present disclosure to provide a method and apparatus for surgical procedures.

A first exemplary embodiment of the present disclosure provides an apparatus for surgical procedures. The apparatus includes a body having a longitudinal axis and a connection opening at a first end of the longitudinal axis, the connection opening including an electrical connection to an electrical circuit maintained within the body and an air path extending through the longitudinal axis of the body. The apparatus further includes a tube assembly having a distal end and a mating end along a tube longitudinal axis, the tube assembly having a vacuum inlet circumscribing an electrode extending from the distal end, the vacuum inlet operable for receiving surgical smoke, the vacuum inlet fluidly connected to an air tube extending through the tube longitudinal axis, the mating end operable to be removably affixed to the connection opening thereby connecting the electrode with the electrical connection and the air path with the air tube. The apparatus still further includes a first button arranged on an external surface of the body operable for controlling a current flow to the electrode at a first level.

A second exemplary embodiment of the present disclosure provides an electrosurgical device. The electrosurgical device includes a tubular body having a longitudinal axis and an electrical rod at a first end of the longitudinal axis, the electrical rod operably coupled to an electrical circuit maintained within the body, the body comprises an air path extending through the longitudinal axis. The electrosurgical device further includes a tube assembly having a distal end and a mating end along a tube longitudinal axis, the tube assembly having a vacuum inlet circumscribing an electrode extending from the distal end, the vacuum inlet operable for receiving surgical smoke, the vacuum inlet fluidly connected to an air tube extending through the tube longitudinal axis, the mating end comprising a socket operable to be removably connected to the electrical rod thereby connecting the air path with the air tube. The electrosurgical device still further includes a first button arranged on an external surface of the body operable for controlling a current flow to the electrode at a first level.

A third exemplary embodiment of the present disclosure provides a method. The method includes providing a body having a longitudinal axis and a connection opening at a first end of the longitudinal axis, the connection opening including an electrical connection to an electrical circuit maintained within the body and an air path extending through the longitudinal axis of the body. The method further includes providing a tube assembly having a distal end and a mating end along a tube longitudinal axis, the tube assembly having a vacuum inlet circumscribing an electrode extending from the distal end, the vacuum inlet operable for receiving surgical smoke, the vacuum inlet fluidly connected to an air tube extending through the tube longitudinal axis, the mating end operable to be removably affixed to the connection opening thereby connecting the electrode with the electrical connection and the air path with the air tube. The method still further includes providing a first button arranged on an external surface of the body operable for controlling a current flow to the electrode at a first level.

The following will describe embodiments of the present disclosure, but it should be appreciated that the present disclosure is not limited to the described embodiments and various modifications of the disclosure are possible without departing from the basic principle. The scope of the present disclosure is therefore to be determined solely by the appended claims.

BRIEF DESCRIPTION OF THE SEVERAL VIEWS OF THE DRAWINGS

FIG. 10 is a perspective view of the device of FIG. 7 shown in the locked position.

FIG. 11 is a perspective view of the device of FIG. 7 shown in the unlocked position.

FIG. 12 is a perspective view of another alternate embodiment of the electrosurgical device.

FIG. 14 is a perspective view of the device of FIG. 12 shown in the locked position.

FIG. 15 is a perspective view of the device of FIG. 12 shown in the unlocked position.

DETAILED DESCRIPTION OF THE INVENTION

Figure 1:
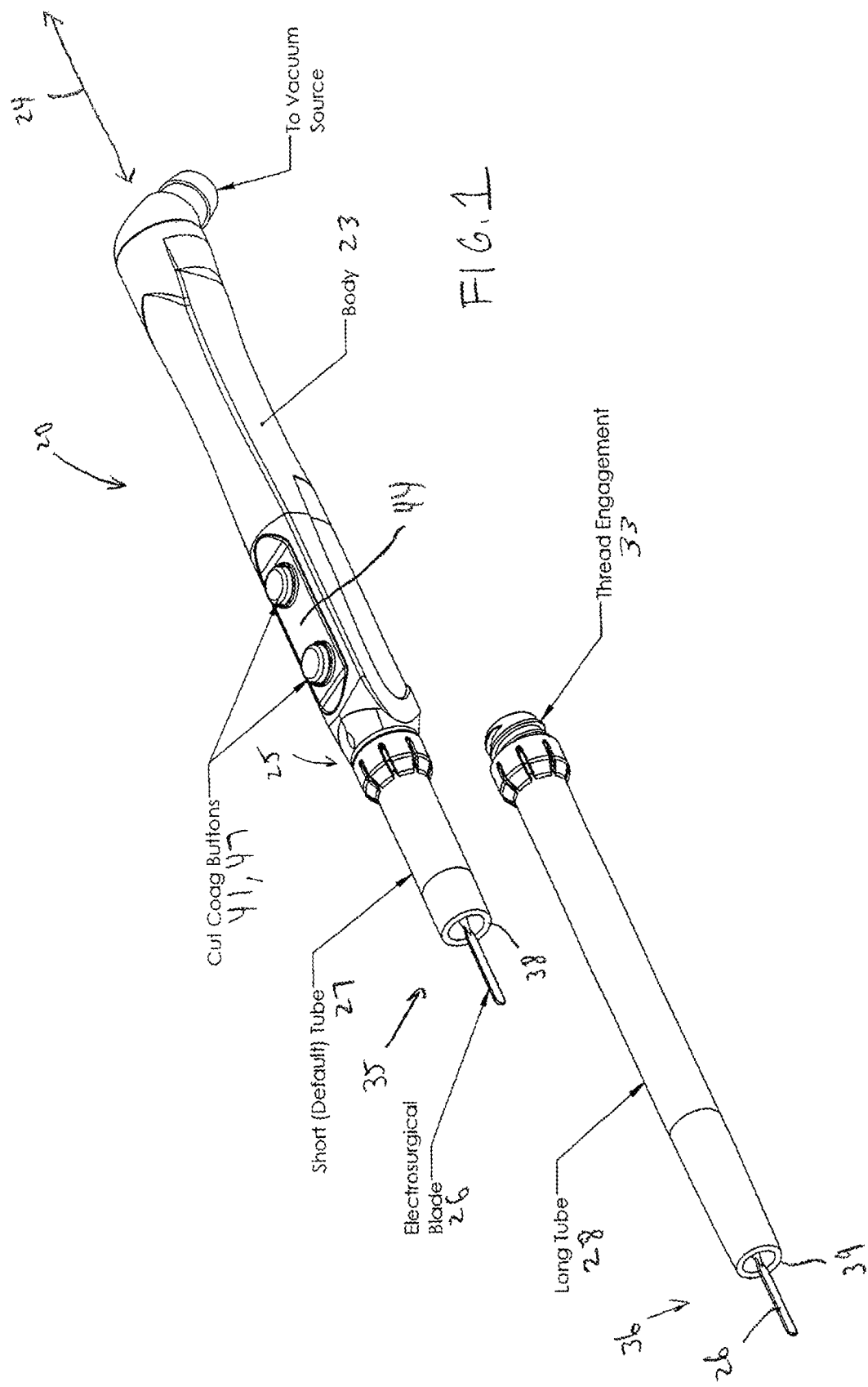
FIG. 1 is a perspective view of a first embodiment of the electrosurgical device of the present invention.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Figure 2:
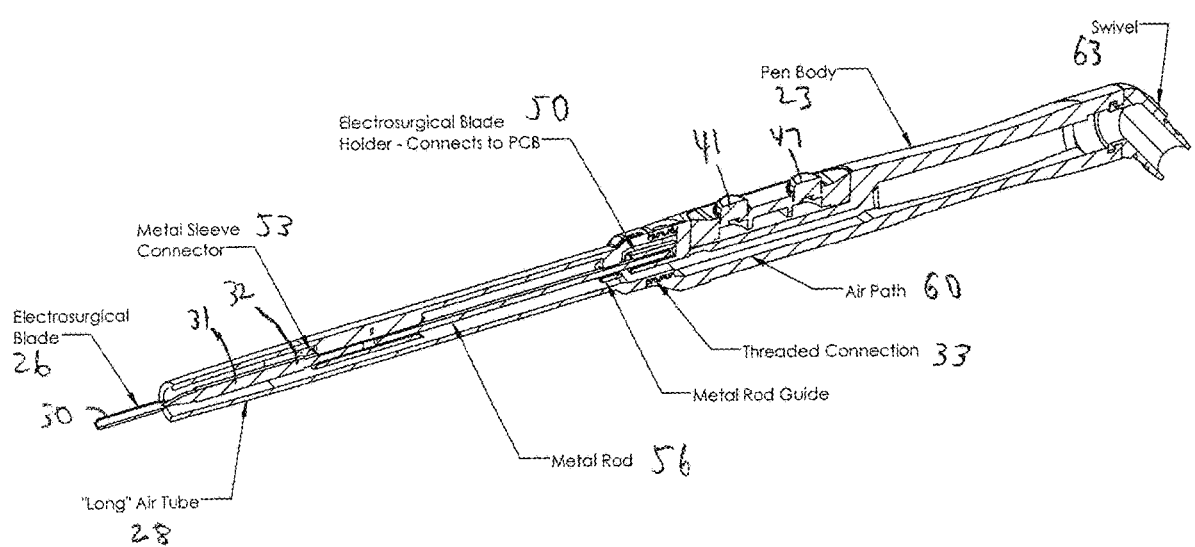
FIG. 2 is a cross-sectional perspective view of the device of FIG. 1.

Referring now to the drawings, and more particularly to FIG. 1 thereof, this invention provides an electrosurgical pen 20 having a body 23. The body 23 may be ergonomically shaped to be received by a user's hand. The body 23 may be pencil shaped and may have a longitudinal axis 24. At the left hand side of the body 23, a threaded opening 25 may receive interchangeable tube assemblies 27 and 28. In FIG. 1, the shorter tube assembly 27 is attached to the body 23. The longer tube assembly 28 is shown separated from the body 23. The tube assemblies 27, 28 have different lengths which may be suitable depending on the surgical site or the preference of the user. The interchangeable tube assemblies change the overall reach of the electrode 26 and the air suction. Various length extensions may be available for each electrosurgical device 20 and each tube assembly may have a built in electrode 26 or the ability to swap the electrode 26, based on the preference of the user. The tube assemblies 27, 28 may surround an electrode 26. The electrode 26 may have a uninsulated end portion 30 (FIG. 2), insulated portion 31 (FIG. 2), and a mounting portion 32 (FIG. 2). At the end of the tube 28, a threaded portion 33 provides a mating surface for engaging with the threaded opening 25 on the body 23. In this manner the tube assemblies 27, 28 may be interchanged. The distal ends 35, 36 of the vacuum tube assemblies 27, 28 comprise inlets 38, 39 for receiving surgical smoke when using the pen 20.

The device 20 may be provided with a first button 41 arranged on the external surface 44 of the body 23. The first button 41 may control the current flow to the device at a first level. The device 20 may have a second button 4 7 for controlling a current flow at a second level to the electrode 26. The current may be provided at different levels depending on the application. For cutting, a higher current level is required, whereas, coagulation requires less current.

Additional buttons may be added for controlling the vacuum source, a light source or the like.

There may be many different lengths for the tubing. Also, the tube may be connected in other ways such as by a mechanical lock or an interference fit.

Turning to FIG. 2, the tube assembly 28 may be removably attached to the body 23 by means of the threaded connection 33. An electrical connection between the printed circuit board and the electrode 26 may be made via a metal rod 56 or strip. The metal rod 56 is electrically connected to the electrode 26 and makes electrical contact with the printed circuit board when the tube assembly 28 is inserted into the end of the body 23. The tube assembly 28 is attached to the body 23 by rotating the tube assembly 28 to engage the threaded connection 33 with the threaded opening 25 at the end of the body 23. As shown, there is an electrode holder 50 that is electrically connected to the printed circuit board to provide power to the electrode 26. The electrode 26 may be received by a metal sleeve connector 53 that is connected to a conductive rod 56. The conductive rod 56 goes into the electrode holder 50 to make the electrical contact with the printed circuit board. The electrode 26 may have an uninsulated end portion 30, an insulated portion 31 and a mounting portion 32 that engages with the metal sleeve connector. The insulated portion 31 may be provided in applications where the user may have a need to remove the electrode 26 and replace it with a different electrode 26.

The tube assembly 28 has a passageway around the electrode 26 for air to pass into the body 23 where it is in fluid communication with an air channel 60 disposed inside the body 23. The body 23 may be provided with a swivel connection 63. The swivel connection 63 may lead to the vacuum source.

Figure 3:
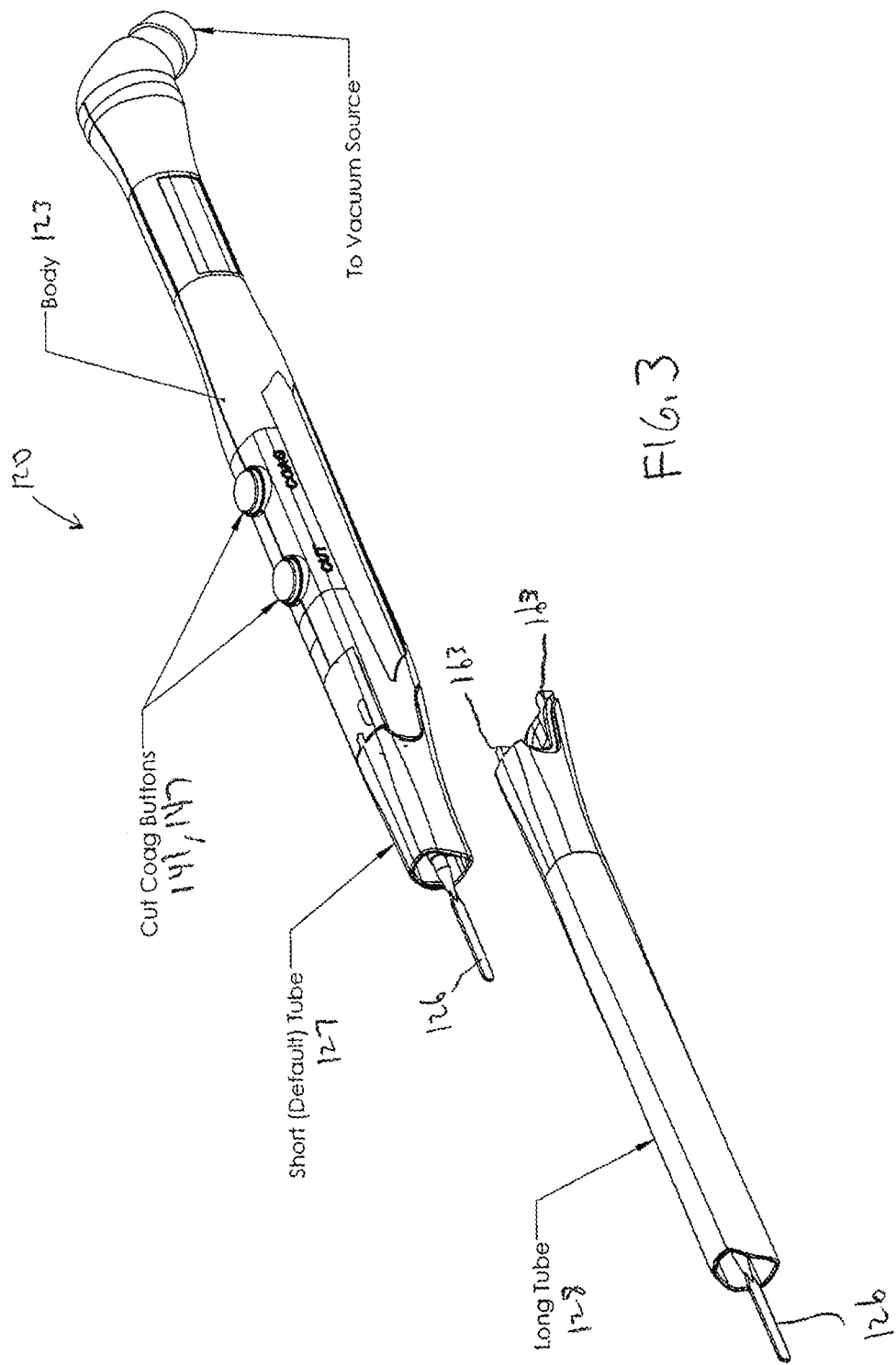
FIG. 3 is a perspective view of an alternate embodiment of the electrosurgical device of the present invention.
Figure 4:
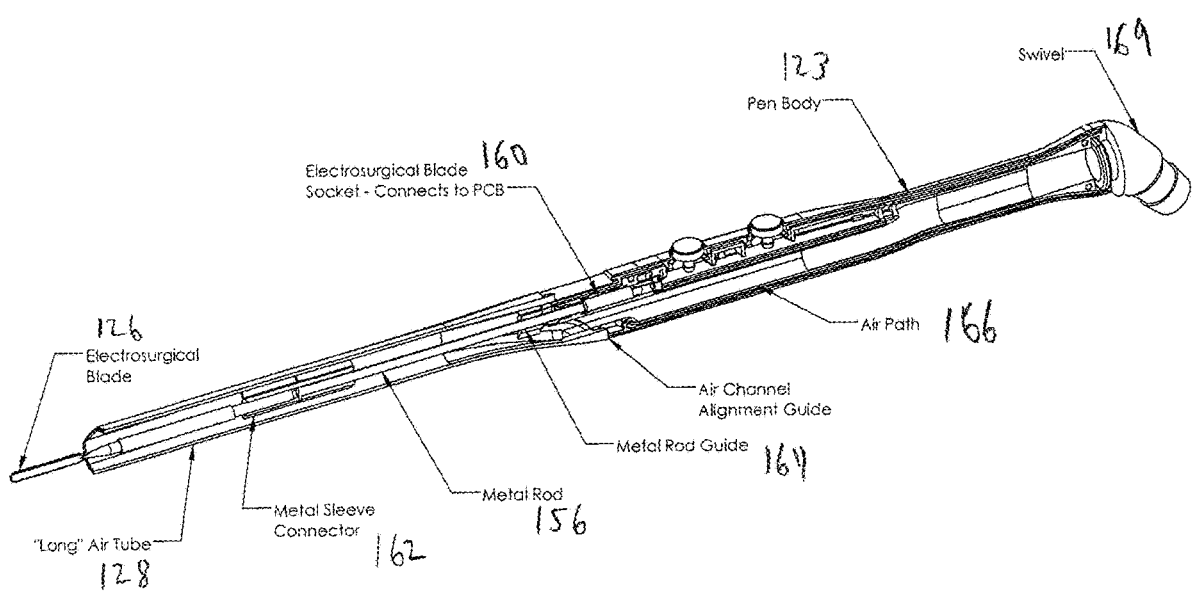
FIG. 4 is a cross-sectional perspective view of the electrosurgical device of FIG. 3.

In an alternate embodiment shown in FIGS. 3-4, an electrosurgical device 120 may utilize a metal contact in order to secure a tube assembly 127 to the body 123 of the electrosurgical device 120. A connecting metal rod 156 (FIG. 4) or strip may span from the electrode 126 in the tube assembly 127 to a blade socket 160 disposed inside the body of the pen 120. The connection between the tube assembly 127 and the body 123 is made by inserting the metal rod 156 into the socket 160. The interface between the electrode 126 and the metal rod 156 may include a metal sleeve connector 162 and a metal rod guide 164. The end 130 of the tube assembly 127 is provided with mating surfaces and one or more alignment guides 163 to provides for correct orientation of the tube assembly 127 with the opening in the body 123. The electrical connection between the electrode 126 and the printed circuit board is made by insertion of the metal rod 156 (which is electrically connected to the electrode 126) into the socket 160 which is electrically connected to the printed circuit board inside the body 123. A long tube 128 containing an electrode 126 is shown separated from the body 123. The mating surfaces and alignment guides 163 are shown on the right hand side of the tube assembly 128. The tube 28 has a passageway for air that is disposed in fluid communication with an air channel 166 disposed in the body 123 of the electrosurgical device 120. The electrosurgical device 123 may also be provided with a swivel connector 169.

Figure 5:
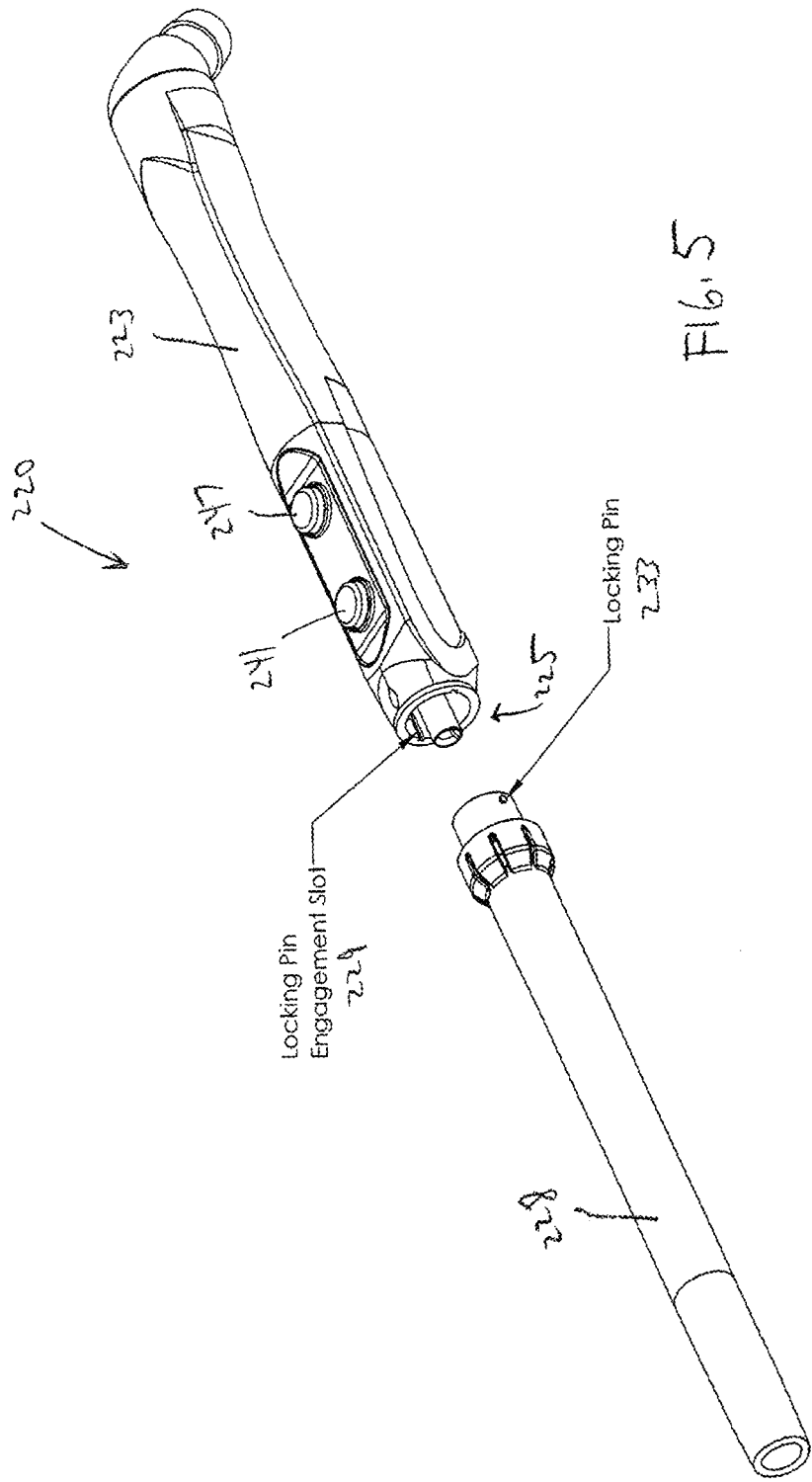
FIG. 5 is a perspective view of another alternate embodiment of the electrosurgical device of the present invention.

In another alternate embodiment shown in FIG. 5, an electrosurgical device 220 has a body 223 with an opening 225 on the left hand side. The opening 225 has a locking pin engagement slot 229 formed therein for receiving a locking pin 233 on the end of a tube assembly 228. The tube assembly 228 receives an electrode 226 and engagement of the tube assembly 228 with the body 223 of the electrosurgical device 220 brings the electrode 226 into electrical contact with the printed circuit board inside the body 223 to connect the electrode 226 to the electrical circuit so that it can be activated by cut and coagulate buttons 241 and 247.

Figure 6:
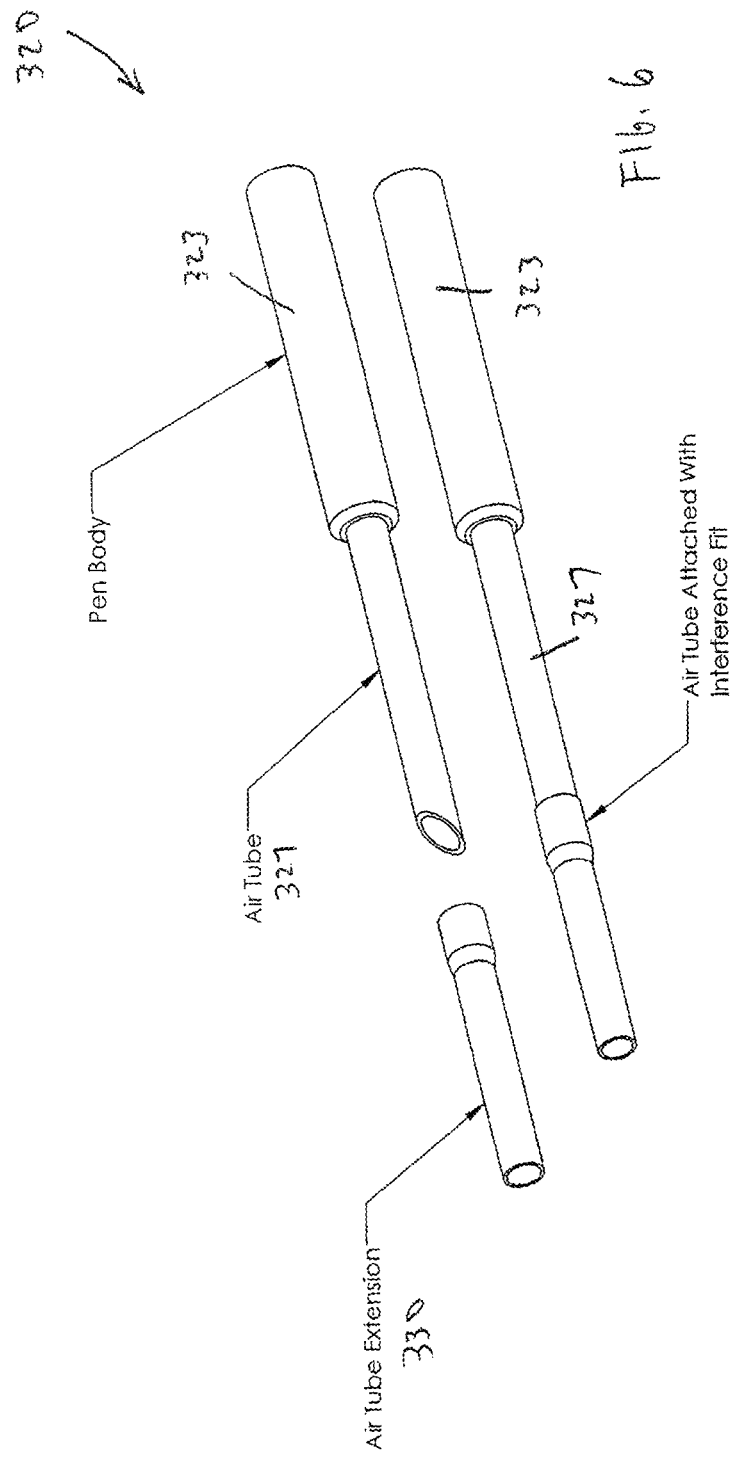
FIG. 6 is a perspective view of a vacuum tube extension.

Turning to FIG. 6, in yet another embodiment of the invention, a tube assembly 327 may be provided with a removable air tube extension 330. The extension 330 may be connected to the end of the tube assembly 327 by means of an interference fit. The extension 330 may also be connected to the tube assembly 327 by means of a mechanical lock. The extension may slide back and forth on the tube 327 to reveal or to hide the electrode 326. The tube assembly 327 is connected to the body 323 of the electrosurgical device 320.

Figure 7:
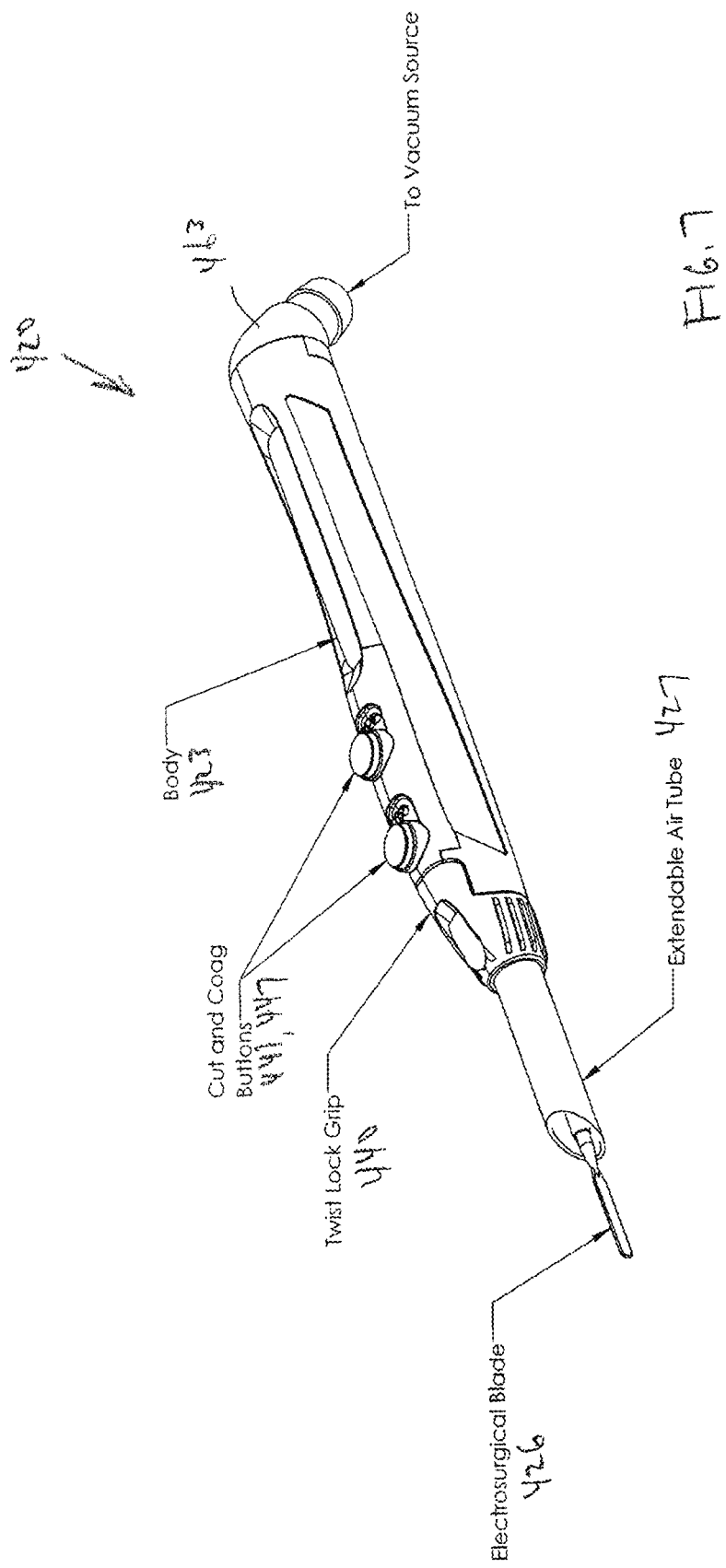
FIG. 7 is a perspective view of another alternate embodiment of the electrosurgical device.
Figure 8:
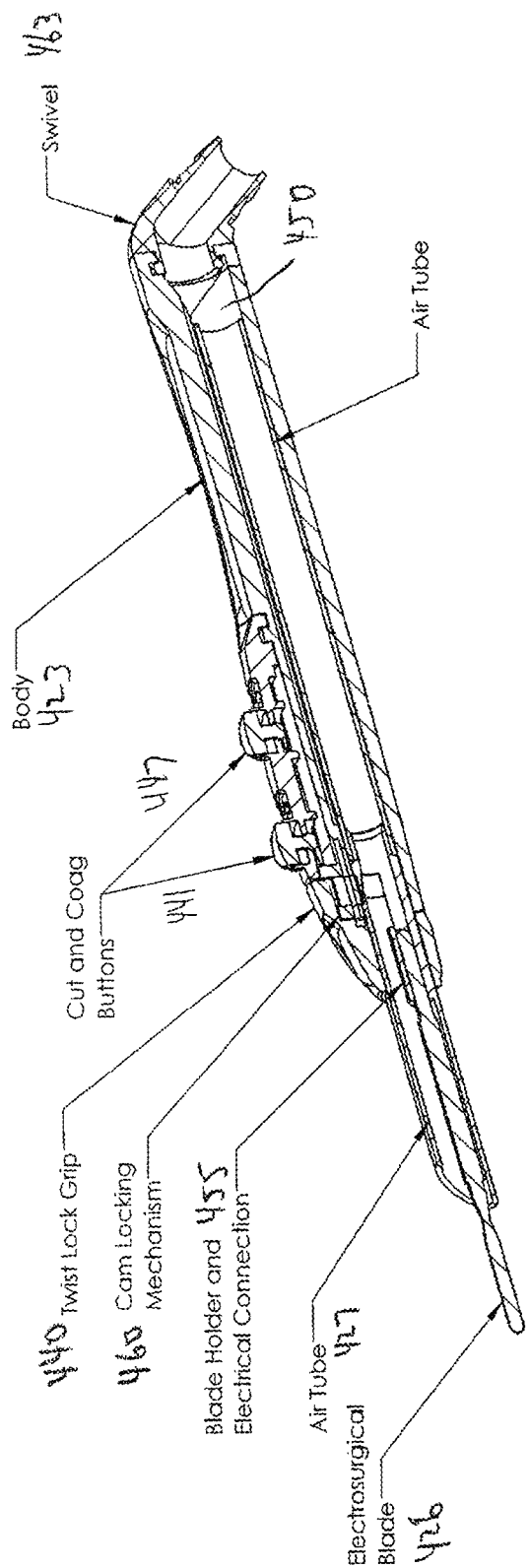
FIG. 8 is a cross-sectional perspective view of the electrosurgical device.

In FIG. 7, another alternate embodiment is shown. As an alternative to the interchangeable tube assemblies, an electrosurgical device 420 includes a telescoping air tube assembly 427 that surrounds an electrode 426. The electrode 426 is mounted on the tube assembly 427 such that movement of the tube assembly also moves the electrode 426 as described below. The tube 427 is received inside the body 423 of the electrosurgical device 420 and may be locked into position by a cam as shown in FIG. 8. The cam may be activated by a twist lock grip 440 disposed at the front of the body 423. The twist lock grip 440 may have ribs 445 disposed thereon to provide for a gripping area for the user.

The electrosurgical device 420 may include buttons 441 and 447 for cutting and coagulating. And the body 423 may include a swivel connector 463 that leads to a vacuum source.

Turning to FIG. 8, the tube 427 extends into a channel 450 inside the body 423 and provides an air pathway disposed in fluid communication with an opening inside the swivel 463 that leads to the vacuum source. The electrode 426 may be disposed inside a blade holder 455. The blade holder 455 is electrically conductive and engages with the end of the electrode 426. The blade holder 455 is electrically connected to the printed circuit board inside the body 423 such that the electrode 426 may be energized by the cut and coagulate buttons when the electrode 426 is disposed in the blade holder 455. Rotation of the twist lock grip 440 actuates a cam locking mechanism 460 (FIG. 9) which provides a frictional engagement between the tube 427 and a cam 469 to prevent the tube 427 from sliding relative to the body 423.

Figure 9:
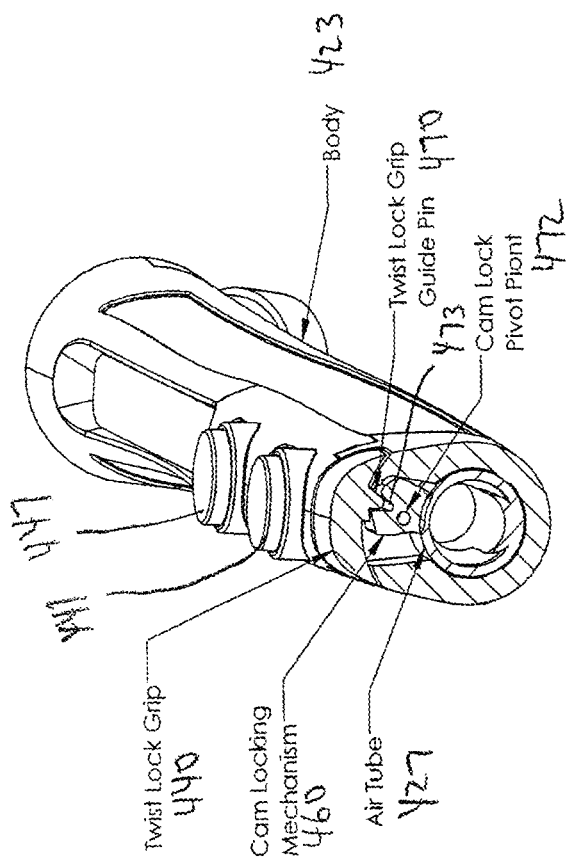
FIG. 9 is a front cross-sectional view of the cam locking mechanism of the device of FIG. 7.

In FIG. 9, the workings of the cam locking mechanism 460 are shown in detail. The cam 469 has an eccentric shape that pivots around a cam lock pivot point 472. Rotation of the cam 469 counterclockwise unlocks the tube 427 (FIG. 11) so that it can be moved relative to the body 423. Rotation of the cam 469 clockwise into the position shown in FIG. 10 causes the cam 469 to engage with the tube 427 to lock it in position. The twist lock grip 440 has a guide pin 470 projecting from an inner surface. The guide pin 470 engages with a slot 473 in the top of the cam 469 such that movement of the twist lock grip 440 from side to side causes rotation of the cam 469 about its pivot point 472. The cam mechanism may be mirrored in the vertical or horizontal direction to provide similar locking properties with actuation in different directions or the cam being on the bottom of the device.

Figure 13:
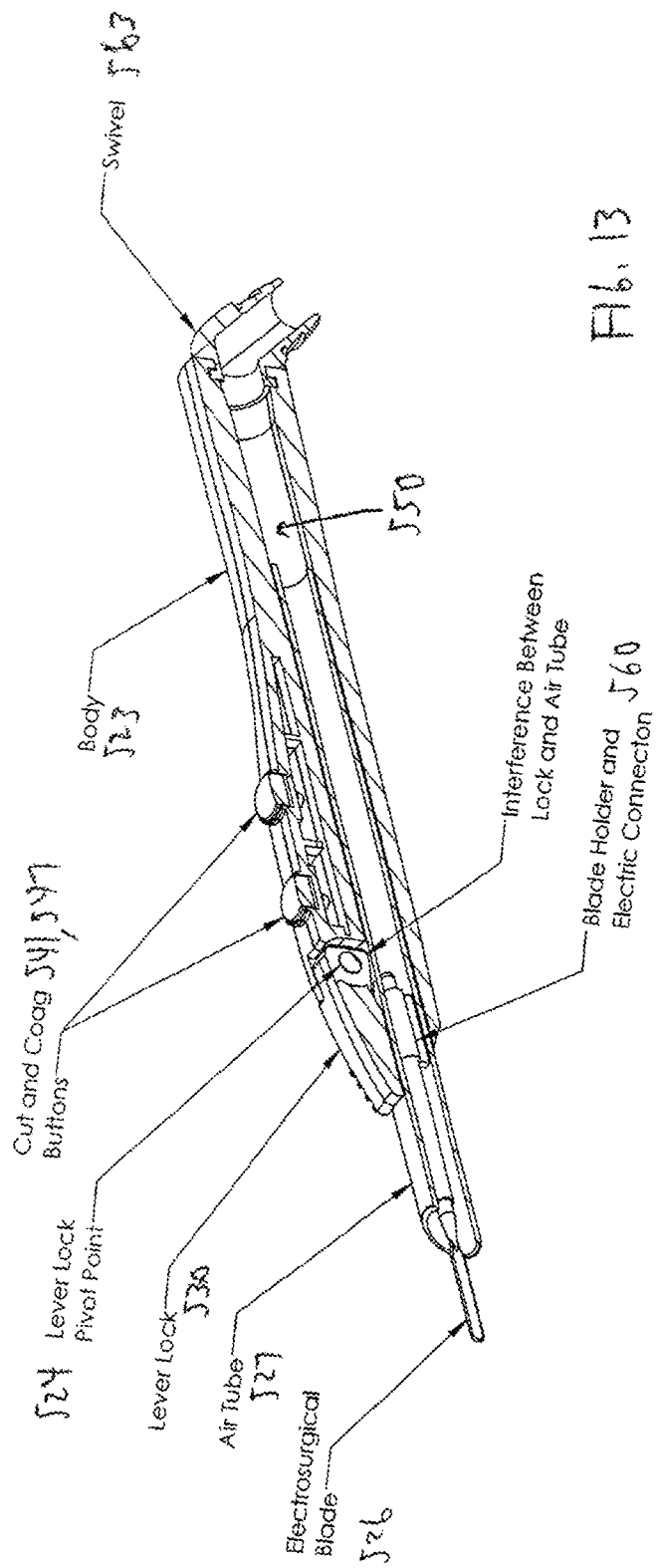
FIG. 13 is a cross-sectional perspective view of the device of FIG. 12.

Turning to FIG. 12, an alternate embodiment for the telescoping tube arrangement of FIGS. 9-10 is shown. Electrosurgical device 520 includes a lever lock 530 that provides for locking and unlocking the tube assembly 527. The lever lock 530 is pivotally attached to the end of the body 523 and pivots about a hinge 524 (FIG. 13). The body 523 may be provided with a swivel 563 at the opposite end that may be connected to the vacuum source. As shown in FIG. 13, the tube 527 is disposed inside a cavity 550 in the body 523 and slides into and out of the cavity 550 to vary the length of the tube 527 extending from the body 523. The electrode 526 may be disposed in the center of the tube 527 in a blade holder 560. The blade holder 560 receives the end of the electrode 526 and makes an electrical connection. The blade holder 560 is constructed of a conductive material and is disposed in electrical communication with the printed circuit board such that insertion of the electrode 526 into the blade holder 560 provides for energizing of the electrode 526 by means of the cut and coagulation buttons 541 and 547. The lever lock 530 pivots about hinge 524. When the lever 530 is pushed downward relative to the body 523, the portion of the lever 530 below the hinge 524 creates interference and engages with the surface of the tube 527 such that the tube 527 is disposed in an unlocked position (FIG. 15). When the lever 530 is raised upward away from the body 523, the portion of the lever 530 below the hinge 524 rotates away from interference with the surface of the tube 527 and the tube 527 may be moved relative to the body 523. The lever mechanism may be present on either side of the device 520 or on the bottom of the device 520. Also, the lever mechanism may be disposed toward the back of the device instead of the front.

Each of the above embodiments may be provided with the following additional features. The electrode may be disposed in the center of the air channel pathway inside the vacuum tube. The electrode may be disposed in the top or bottom of the air channel pathway inside the vacuum tube. The electrode may be disposed in the wall of the air channel pathway. This arrangement may split the air channel so that half of the electrode is located within the air channel while the other half of the electrode is outside of the air channel. The vacuum tube may have various "cut" angles on its distal end in order to improve performance. The inlet of the vacuum tube may be angled such that inlet is parallel to the line of sight of the user when the device is in use. Also, overmold or rubberized features may be added to the body of the electrosurgical devices to improve grip and comfort. The buttons may have various configurations including different shapes, a rocker switch, different colors or an overmold. The body of the device may be illuminated to help the user see the buttons or other features of the pen. This may be accomplished via an exposed light source or through a clear air tube which would act as a light tube. The light source may be electrically powered or made possible with photoluminescent paint. In addition, the device may include a caddy for extra electrodes or tubes. This holder may attach to the pen, the hose, or may be detached to affix onto somewhere in the surgical theater.

The present invention contemplates that many changes and modifications may be made. Therefore, while the presently-preferred form of the electrosurgical device has been shown and described, and several modifications and alternatives discussed, persons skilled in this art will readily appreciate that various additional changes and modifications may be made without departing from the spirit of the invention, as defined and differentiated by the following claims.

The invention claimed is:

1. An apparatus for surgical procedures, the apparatus comprising:
   a body having a longitudinal axis and a connection opening at a first end of the longitudinal axis, the connection opening including an electrical connection to an electrical circuit maintained within the body and an air path extending through the longitudinal axis of the body, the air path defining a channel fluidly connecting the connection opening at the first end to a swivel connector located at a second end of the longitudinal axis of the body;
   a tube assembly having a distal end and a mating end along a tube longitudinal axis, the tube assembly having a vacuum inlet circumscribing an electrode extending from the distal end, the vacuum inlet operable for receiving surgical smoke, the vacuum inlet fluidly connected to an air tube extending through the tube longitudinal axis, the mating end operable to be removably affixed to the connection opening thereby connecting the electrode with the electrical connection and the air path with the air tube, the tube assembly operable to slidably move to a plurality of locations within the channel of the body, wherein each one of the plurality of locations vary a length of the tube assembly extending from the body and vary a distance of a distal end of the electrode from the body, wherein the electrode slidably moves with the tube assembly with respect to the body;

a first button arranged on an external surface of the body operable for controlling a current flow to the electrode at a first level;

a rotatable cam comprising a grip body that circumscribes the body and is located on the connection opening of the body, the rotatable cam operable to pivot about a lock pivot point in response to the grip body twisting about the body to a locked position and an unlocked position, the rotatable cam comprising a top exterior body including a guide pin projecting from an inner surface of the top exterior body, the guide pin operable to engage a slot in the lock pivot point when the rotatable cam is in the locked position; and a removable air tube extension operable to be slidably coupled to the distal end of the tube assembly, the removable air tube operable to circumscribe an entire length of the electrode, wherein the removable air tube, the vacuum inlet, the channel and the swivel connector located at the second end are fluidly connected, wherein the lock pivot point is operable to engage and maintain a location of the removable air tube in the locked position, and wherein the lock pivot point does not engage the removable air tube in the unlocked position.

2. The apparatus according to claim 1, the apparatus further comprising a second button arranged on the external surface of the body operable for controlling the current flow to the electrode at a second level, wherein the second level is greater than the first level.

3. The apparatus according to claim 1, the electrode comprises metal rod or strip for connecting to the electrical connection.

4. The apparatus according to claim 1, wherein the connection opening is one of a mechanical lock and an interference fit.

5. The apparatus according to claim 1, the body further comprising a swivel connection operably coupled to the air path, the swivel connection operable for connecting to a vacuum source operable for pulling air through the air path and the air tube.

6. The apparatus according to claim 1, wherein the vacuum inlet is angled parallel to a line of sight of a user.

7. The apparatus according to claim 1, the apparatus further comprising a light source operable to illuminate the body and the first button.

8. An electrosurgical device, the electrosurgical device comprising:

a tubular body having a longitudinal axis and an electrical rod at a first end of the longitudinal axis, the electrical rod operably coupled to an electrical circuit maintained within the body, the body comprises an air path extending through the longitudinal axis, the air path defining a channel fluidly connecting the connection opening at the first end to a swivel connector located at a second end of the longitudinal axis of the body;

a tube assembly having a distal end and a mating end along a tube longitudinal axis, the tube assembly having a vacuum inlet circumscribing an electrode extending from the distal end, the vacuum inlet operable for receiving surgical smoke, the vacuum inlet fluidly connected to an air tube extending through the tube longitudinal axis, the mating end comprising a socket operable to be removably connected to the electrical rod thereby connecting the air path with the air tube, the tube assembly operable to slidably move to a plurality of locations within the channel, wherein each one of the plurality of locations vary a length of the tube assembly extending from the first end of the tubular body and vary a distance of a distal end of the electrode from the body, wherein the electrode slidably moves with the tube assembly with respect to the body;

a first button arranged on an external surface of the body operable for controlling a current flow to the electrode at a first level;

a rotatable cam comprising a grip body that circumscribes the body and is located on the connection opening of the body, the rotatable cam operable to pivot about a lock pivot point in response to the grip body twisting about the body to a locked position and an unlocked position, the rotatable cam comprising a top exterior body including a guide pin projecting from an inner surface of the top exterior body, the guide pin operable to engage a slot when the rotatable cam is in the locked position; and a removable air tube extension operable to be slidably coupled to the distal end of the tube assembly, the removable air tube operable to circumscribe an entire length of the electrode, wherein the removable air tube, the vacuum inlet, the channel and the swivel connector located at the second end are fluidly connected, wherein the lock pivot point is operable to engage and maintain a location of the removable air tube in the locked position, and wherein the lock pivot point does not engage the removable air tube in the unlocked position.

9. The electrosurgical device according to claim 8, the tube assembly further comprising at least one alignment guide extending from the mating end operable to interface with corresponding mating surfaces on the tubular body.

10. The electrosurgical device according to claim 9, wherein the at least one alignment guide and the corresponding mating surfaces provide a correct orientation of the tubular body relative to the tube assembly.

11. The electrosurgical device according to claim 8, the body further comprising a swivel connection operably coupled to the air path, the swivel connection operable for connecting to a vacuum source operable for pulling air through the air path and the air tube.

12. The electrosurgical device according to claim 8, wherein the electrode with the distal end of the tubular assembly is moveably extendable relative the body along the tubular longitudinal axis.

13. A method comprising:

(a) providing a body having a longitudinal axis and a connection opening at a first end of the longitudinal axis, the connection opening including an electrical connection to an electrical circuit maintained within the body and an air path extending through the longitudinal axis of the body, the air path defining a channel fluidly connecting the connection opening at the first end to a swivel connector located at a second end of the longitudinal axis of the body;

(b) providing a tube assembly having a distal end and a mating end along a tube longitudinal axis, the tube assembly having a vacuum inlet circumscribing an electrode extending from the distal end, the vacuum inlet operable for receiving surgical smoke, the vacuum inlet fluidly connected to an air tube extending through the tube longitudinal axis, the mating end operable to be removably affixed to the connection opening thereby connecting the electrode with the electrical connection and the air path with the air tube, the tube assembly operable to slidably move to a plurality of locations within the channel of the body, wherein the vacuum inlet, the channel and the swivel connector located at the second end are fluidly connected, wherein each one of the plurality of locations vary a length of the tube assembly extending from the body and vary a distance of a distal end of the electrode from the body, wherein the electrode slidably moves with the tube assembly with respect to the body;

(c) providing a rotatable cam comprising a grip body that circumscribes the body and is located on the connection opening of the body, the rotatable cam operable pivot about a lock pivot point in response to the grip body twisting about the body to a locked position and an unlocked position, wherein the lock pivot point is operable to engage and maintain a location of the tube assembly in the locked position, and wherein the lock pivot point does not engage the removable air tube in the unlocked position; and (d) providing a first button arranged on an external surface of the body operable for controlling a current flow to the electrode at a first level.

14. The method according to claim 13, the method further comprising providing a second button arranged on the external surface of the body operable for controlling the current flow to the electrode at a second level, wherein the second level is greater than the first level.

15. The method according to claim 13, wherein the connection opening is one of a threaded connection, a mechanical lock and an interference fit.

16. The method according to claim 13, the body further comprising a swivel connection operably coupled to the air path, the swivel connection operable for connecting to a vacuum source operable for pulling air through the air path and the air tube.

17. The method according to claim 13, wherein the vacuum inlet is angled parallel to a line of sight of a user.

* * * * *